United States Patent [19]

Tanikawa

[11] Patent Number: 4,584,663
[45] Date of Patent: Apr. 22, 1986

[54] APPARATUS FOR POWER-ON DATA INTEGRITY CHECK OF INPUTTED CHARACTERS STORED IN VOLATILE MEMORY

[75] Inventor: Kowji Tanikawa, Tokyo, Japan

[73] Assignee: Olympus Optical Co., Ltd., Tokyo, Japan

[21] Appl. No.: 615,704

[22] Filed: May 29, 1984

Related U.S. Application Data

[63] Continuation of Ser. No. 295,870, Aug. 25, 1981, abandoned.

[30] Foreign Application Priority Data

Oct. 3, 1980 [JP] Japan ................... 55-138486

[51] Int. Cl.⁴ ............ G06F 7/00; G06F 7/20; G06F 11/00
[52] U.S. Cl. ................... 364/900; 365/201; 365/228; 371/21
[58] Field of Search ... 364/200 MS File, 900 MS File, 364/705; 235/463; 382/13, 20, 34, 41; 365/226, 228, 201; 340/735; 371/21, 57, 67

[56] References Cited

U.S. PATENT DOCUMENTS

| | | | |
|---|---|---|---|
| 3,794,818 | 2/1974 | Kennedy | 235/153 AM |
| 3,918,028 | 11/1975 | Humphrey et al. | 340/146.3 F |
| 3,940,601 | 6/1976 | Henry et al. | 235/153 AC |
| 4,054,911 | 10/1977 | Fletcher et al. | |
| 4,094,001 | 6/1978 | Miller | 364/900 |
| 4,110,737 | 8/1978 | Fahey | 340/146.3 Q |
| 4,118,789 | 10/1978 | Casto et al. | 364/900 |
| 4,143,356 | 3/1979 | Nally | 340/146.3 Q |
| 4,145,761 | 3/1979 | Gunter et al. | 365/227 |
| 4,181,909 | 1/1980 | Pyeatte et al. | 375/107 |
| 4,199,677 | 4/1980 | Vanderpool | 235/463 |
| 4,239,151 | 12/1980 | Enser et al. | 235/437 |
| 4,241,409 | 12/1980 | Nolf | 364/705 |
| 4,247,913 | 1/1981 | Hiniker et al. | 365/228 |
| 4,339,801 | 7/1982 | Hosaka et al. | 364/431.04 |
| 4,363,124 | 12/1982 | Aichelmann, Jr. | 371/21 |
| 4,375,663 | 3/1983 | Arcara | 364/200 |
| 4,380,068 | 7/1983 | De Couasnon | 371/24 |
| 4,414,545 | 11/1983 | Sakurada et al. | 340/790 |

FOREIGN PATENT DOCUMENTS

2013378 8/1979 United Kingdom .

OTHER PUBLICATIONS

*IBM Technical Disclosure Bulletin*, vol. 20, No. 10, Mar. 1978, pp. 4071-4072, M. E. Chamoff et al.: "Nonvolatile Totals Implementation".

*Primary Examiner*—James D. Thomas
*Assistant Examiner*—A. Williams
*Attorney, Agent, or Firm*—Frishauf, Holtz, Goodman & Woodward

[57] ABSTRACT

A memory data coincidence device includes a volatile read write memory connected to a main power source and auxiliary backup power source, and a keyboard for supplying data to the read write memory. The device further includes a read only memory for storing all data capable of being stored in the read write memory and a central processor unit (CPU) which compares the data of the read write memory with all data of the read only memory before it reads data out of the read write memory. If no coincidence takes place, the CPU sends forth a signal denoting the condition that the read write memory is not backed up.

7 Claims, 4 Drawing Figures

F I G. 1
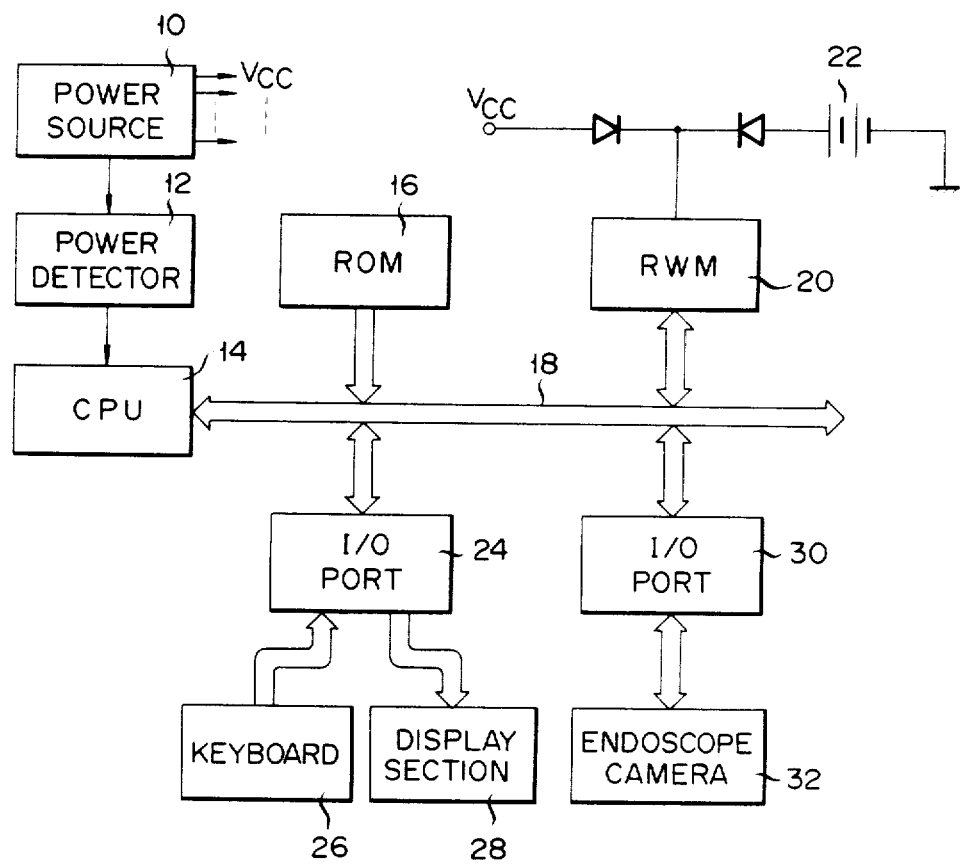

FIG. 3

| | |
|---|---|
| 45 | E |
| 41 | A |
| 32 | 2 |
| 34 | 4 |
| 20 | ␣ |
| 53 | M |
| 54 | 4 |
| 30 | 0 |

FIG. 4

| | |
|---|---|
| 30 | 0 |
| 31 | 1 |
| ⋮ | ⋮ |
| 38 | 8 |
| 39 | 9 |
| 41 | A |
| 42 | B |
| ⋮ | ⋮ |
| 59 | Y |
| 5A | Z |
| 2B | + |
| 2D | − |
| 20 | ␣ |

APPARATUS FOR POWER-ON DATA INTEGRITY CHECK OF INPUTTED CHARACTERS STORED IN VOLATILE MEMORY

This application is a continuatioin of application Ser. No. 295,870, filed Aug. 25, 1981, now abandoned.

BACKGROUND OF THE INVENTION

This invention relates to a memory device which can store data even when a main power source is cut off.

Recently, microprocessors are applied to various control operations, such as for adjustment of a desired temperature and the automatic selection of a television channel. With such control device, it is necessary to store data relating to the control conditions, in a read wirte memory. The read write memory is a volatile memory, therefore, some precautionary measures should be taken in case of momentary power failure. Until now, an auxiliary power source (cell or large capacitor) has been connected to the read write memory in order to retain stored data, thereby carrying out the so-called backup process of preventing stored data from being extinguished even when the main power source is cut off. The period is limited, in which the backup process can be continued by a cell or capacitor. Upon lapse of the period, the contents of the memory disappear. Further, even during the backup period, externally generated noises sometimes change the contents of the memory. Where the contents of a memory disappear or are changed, then the control device which carries out various forms of control in accordance with the memory contents, tends to malfunction. As a result, an unexpected accident happens, depending on the type of object device or instrument whose operation should be controlled. In the case of CPU control, the CPU would give rise to an erroneous results.

SUMMARY OF THE INVENTION

It is accordingly the object of the present invention to provide a memory device which can detect any change in altered stored data and prevents altered data from being read out.

To attain the above-mentioned object, the invention provides a memory device which comprises a data-specifying means, a read write memory for storing data specified by the data-specifying means, a read only memory for storing all data capable of being specified by the data-specifying means, and a judgment circuit for reading data from the read write memory and read only memory, comparing the output data from the read write memory with all the output data from the read only memory, and where coincidence does not arise between both output data, issuing a signal denoting noncoincidence.

BRIEF DESCRIPTION OF THE DRAWINGS

FIG. 1 is a block diagram of an endoscrope type photographing system provided with a memory device embodying the present invention;

FIG. 3 shows data stored in a read write memory; and

FIG. 4 indicates data stored in a read only memory.

DETAILED DESCRIPTION OF THE PREFERRED EMBODIMENT

Figure 2:
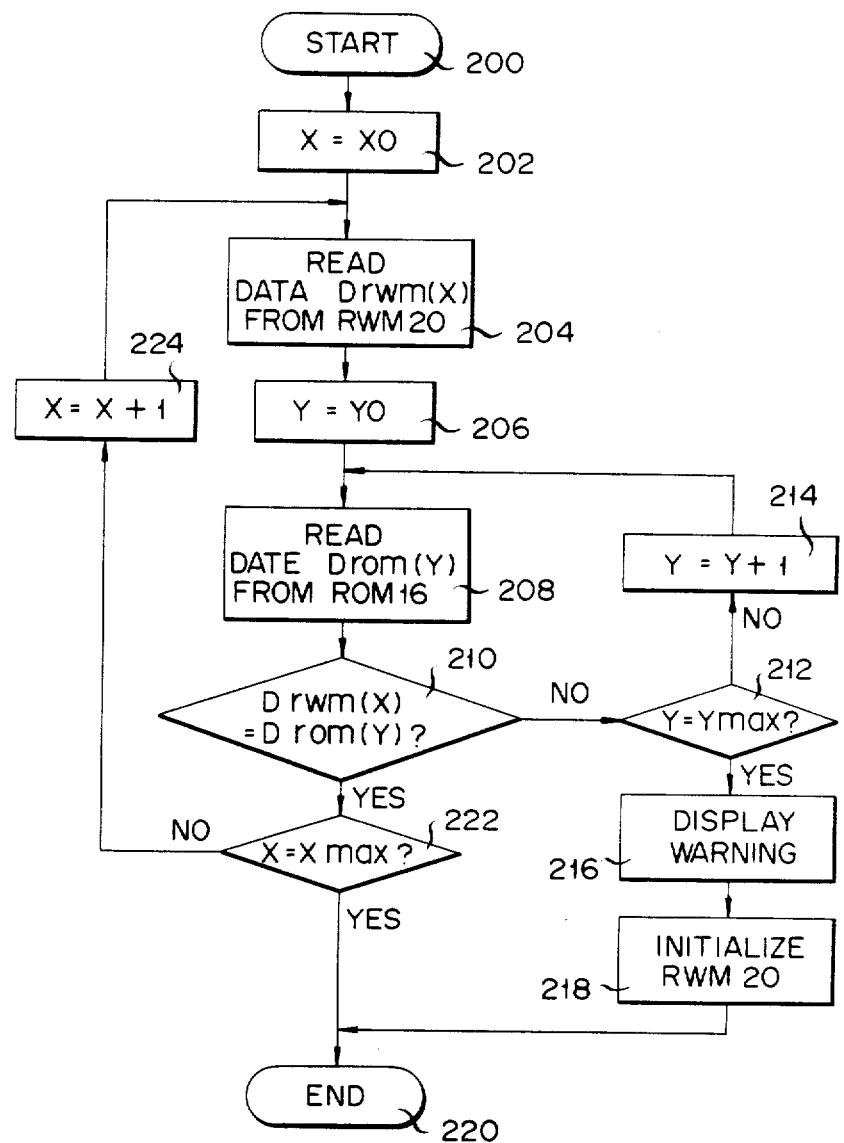
FIG. 2 is a flow chart showing the operation of the photographing system.

Description is now given with reference to the accompanying drawings of a memory device embodying the present invention. FIG. 1 is a block diagram of a data photographing system for an endoscope camera which is provided with the memory device embodying the invention. A main power source 10 for supplying power VCC to the respective parts of the photographing system is connected to a power detector 12, an output from which is supplied to a central processor unit (CPU) 14. The CPU controls the whole operation of the photographing system including the photographing of data. A control program for this purpose is stored in a nonvolatile read only memory (ROM) 16, which is connected to the CPU 14 by means of a data bus 18. A read write memory (RWM) 20 for temporarily storing data required for the above-mentioned control is also connected to the data bus 18. The volatile RWM 20 is supplied with not only power from the main power source 10 but also from an auxiliary cell-type power source 22 used to hold data. A keyboard 26 for specifying data, and display section 28 are connected ot the data bus 18 through an I/O port 24. An endoscope camera 32 whose operation is to be controlled is also connected to the data bus 18 through an I/O port 30.

Description is now given of the operation of the photgraphing system of the endoscope camera. The endoscrope camera 32 photographs the coeliac condition of a patient and together with required data such as the kind of endoscope, the identity of the patient, the site of photographing, and the like on the same film frame. If data are specified each time a frame is photographed, then the operation of the endoscope camera is interrupted during this period. Such interuption is objectionable, because a patient into whose coeliac cavity an endoscope is inserted suffers an increased amount of pain. It is therefore preferred that all data be specified by means of the keyboard 26 before the photographing of the first frame, and then stored in the RWM 20. The data is generally held by the main power source VCC. The main power source VCC is normally provided in a light source section of the endoscope photographing system. Power from the main power source VCC is conducted through the endoscope body to the photographing system. An endoscope is sometimes exchanged for a different type, depending on the position of the patient's coeliac cavity which is to be photographed. Since, at this time, the phtographing system is separated from the light source including the main power source VCC, the RWM 20 is shut off from the main power source VCC. Power is supplied from the auxiliary power source 22 instead of from the main power source VCC. When the data photographing system is again connected to the light source through the endoscope, then the RWM 20 holds the data by the power supplied from the main power source VCC.

The CPU 14 performs a control program stored in the ROM 16 in accordance with the data stored in the RWM 20. Now let it be assumed that when the CPU 14 is supplied with power, then the photographing of the patient's coeliac condition and the related data photographing is automatically commenced. Where, in this case, data previously stored in the RWM 20 is extinguished or changed, then the photographing system malfunctions. Description is now given with reference to the flow chart of FIG. 2 of the process of preventing the malfunction of the photographing system.

Assuming that data to be photographed is formed of 8 bytes, for example, of the EA24    M40 pattern (where    means a blank). Further, let it be assumed that the first 6 bytes represent data to be photographed with respect to the patient, endoscope, etc., and the remaining 2 bytes denote data on the serial number of a film frame. The above-mentioned 8 bytes data is converted into ASCII code of 1 letter-1 byte. The converted data is stored in the RWM 20 as illustrated in FIG. 3. Now let it be assumed that data characters to be photographed total 39 forms, including the digits from 0 to 9, the alphabet letters from A to Z and notations such as +, − and  . These data characters are stored in the ROM 16 in the form of a ASCII of 1 bytes as illustrated in FIG. 4. In FIGS. 3 and 4, numerals indicated in the squares constitute the ASCII code. The characters on the right side thereof represent the actual characters.

As previously mentioned, when supplied with power, the CPU 14 automatically performs a prescribed control program. If data stored in the RWM 20 is ascertained before the execution of the program, then the subject memory device will not malfunction. When the power detector 12 detects the supply of power from the main power source 10, then the CPU 14 commences the execution of a data ascertaining program shown in FIG. 2. At step 202 following start step 200, the read address X of the RWM 20 is set at an intial value of XO. At step 204, data Drwm (XO) is read out of the XO address of the RWM 20. With the foregoing embodiment, E, that is, 45 of the ASCII code is first read out. At step 206, the address Y of the ROM 16 is set at an initial value of YO. At step 208, data Drom (YO) is read out of the YO address of the ROM 16. With the foregoing embodiment, the data Drom (YO) denotes 0, that is, 30 of the ASCII code. At step 210, comparison is made between the data Drwm (XO) and the data Drom (YO). Where data previously stored in the RWM 20 is extinguished or changed, coincidence will never take place between these data Drwm (XO) and Drom (YO). Where normal data is stored in the RWM 20, then coincidence of data will never fail to be attained by shifting the addresses of the ROM 16 one after another, even when the data Drwm (XO) is not equal to the data Drom (YO). Where no coincidence arises between the data Drwm (XO) and Drom (YO), then a judgment is made at step 212 as to whether the read address Y of the ROM 16 represents a maximum address Ymax. If Y = Ymax is not realized, then the address Y is incremented at step 214, and step 208 is again taken. Y = Ymax means that no coincidence takes place between the data stored in the RWM 20 and all the data stored in the ROM 16, that is, data stored in the RWM 20 was not normal. In such case, the display section 28 gives a warning at step 216. Then, the user is advised to suspend the operation of the CPU 14 by a look at the indication on the display section 28 and to supply fresh data to the RWM 20. At this time, the CPU 14 causes the data of the RWM 20 to be set at an initial value. The reason is that when a change takes place in data on the number of film frames, for example, when the film end is to be detected, then the memory device is likely to manlfunction, and consequently data on the number of film frames is set at a minimum value of zero or a maxium value.

When, at step 210, coincidence is judged to take place between the data stored in the RWM 20 and the data stored in the ROM 16, then it is provided that data stored in the RWM 20 is normal and is not extinguished or changed. At step 222, therefore, a judgment is made as to whether all data have been read out of the RWM 20, according to whether the read address X of the RWM 20 has a maximum value of Xmax or not. If X = Xmax is not realized, the address X is incremented at step 224, and later step 204 is taken again. If X = Xmax results, it means that all data stored in the RWM 20 are correct. Consequently, the operation proceeds to a main routine through an end step 220.

After all the data stored in the RWM 20 are judged to be effective, the CPU 14 causes all these data and the image of a foreground subject to be photographed together. Therefore, when the RWM 20 is shut off from the main power source 10, and the memory data is retained only by power supplied from the auxiliary power source 22, should data stored in the RWM 20 be extinguished, the extinction can be detected, preventing the CPU 14 from carrying out erroneous control. Further, where data stored in the RWM 20 are changed due to the occurrence of noise signals, though not extinguished, it is possible to detect any change in any other data from that stored in the ROM 16.

With the foregoing embodiment, a volatile memory is backed up by power supplied from an auxiliary power source. However, it is possible to back-up the volatile memory, for example, by a capacitor. Further, it is possible to ascertain the effectiveness of data stored in the volatile memory not only while it is backed up by the auxiliary power source but also while it is supplied with power by the main power source. In such case, it is advisable to let the CPU 14 perform the program of FIG. 2 not only when power supply from the main power source is detected, but also as often as required. Then it is unnecessary to provide the power supply detector 12. Should an abnormal condition occur in the subject memory device, it is advisable to give an alarm or lock the memory device out of operation. It is not always necessary to set the data sotred in the RWM 20 at an initial value.

The present invention is applicable to devices other than a camera. Namely, the invention can be applied in selecting a television channel, in recording data on a video tape or adjusting a cooler temperature. Obviously, this invention is applicable also to the nonvolatile type RWM.

What is claimed is:

1. A memory arrangement for use in a data processing system for processing data to control an object device, wherein a number of different predetermined data characters can be used in the control of the device, comprising:

input means for inputting selected ones of the predetermined data characters required for controlling the object device;

volatile read/write memory means connected to a main power source and to an auxiliary power source for storing the selected data characters inputted by said input means;

nonvolatile read only memory means for storing all of the different predetermined data characters which can be used for controlling the object device;

means for reading the selected data characters from said read/write memory means and for processing the read data to control the object device; and means coupled to said main power souce, for comparing each of the selected data characters from said read/write memory means with each one of the different predetermined data characters stored in said read only memory means until a match is found or all the stored data characters have been tested, each time said main power source is turned on, and for producing a noncoincidence signal in the absence of a coincidence between any of the selected data characters read from said read/write memory means and any one of the data characters stored in said read only memory means.

2. A memory arrangement for use in apparatus for controlling an object device, wherein a number of different predetermined data characters can be used in the control of the device, comprising:

input means for inputting selected ones of the predetermined data characters required to be processed to control the object device;

volatile read/write memory means connected to said input means and to external main and auxiliary power sources for storing the selected data characters inputted by said input means;

nonvolative read only memory means connected to the main power source for storing all of the different predetermined data characters which can be used for controlling to object device; and microprocessor means connected to the main power source for reading the selected data characters from said volatile read/write memory means to process the read data and to control the object device each time the main power source is turned on, for comparing each of the selected data characters read from said read/write memory means with each one of the different predetermined data characters stored in said nonvolatile read only memory means until a match is found or all the stored data characters have been tested, each time the main power source is turned on, and for inhibiting data processing in the absence of a coincidence between any of the selected data characters and any one of the data characters stored in the nonvolatile read only memory means.

3. A data processing system according to claim 1, including an endoscope forming the object device.

4. An apparatus according to claim 2, including an endoscope forming the object device.

5. A memory arrangement with a data backup checking function, comprising:

a main power source;

an auxiliary power source;

volatile memory means connected to said main power source and to said auxiliary power source;

input means, connected to said volatile memroy means, for inputting and storing certain data characters into said volatile memory means;

nonvolatile memory means for storing all data characters capable of being input by said input means, up to a given number of said certain characters; and judging means connected to said main power source, said volatile memory means and to said nonvolatile memory means, for sucessively comparing each data character stored in said volatile memory means with each data character stored in said nonvolatile memory means until a match is found or all the stored data characters have been tested, each time said main power source is placed on, and for emitting a detection signal in the absence of a coincidence between said each data character stored in said volatile memory means and said data characters stored in said nonvolatile memory means.

6. The memory device according to claim 1, wherein said comparing means is connected to said main power source, and energized by power supplied therefrom.

7. The memory device according to claim 1, which further comprises:

display means which is connected to said comparing means for emitting a warning in response to the noncoincidence signal; and means which is connected to said comparing means and read write memory means for setting said read write memory means at predetermined data in response to the noncoincidence signal.

* * * * *